United States Patent [19]
Moreau

[11] Patent Number: 6,007,818
[45] Date of Patent: *Dec. 28, 1999

[54] OLIGOSACCHARIDE DERIVED FROM AN ANTIGENIC POLYSACCHARIDE OBTAINED FROM A PATHOGENIC AGENT

[75] Inventor: Monique Moreau, Lyons, France

[73] Assignee: Pasteur Merieux Serums Et Vaccines, Lyon, France

[*] Notice: This patent is subject to a terminal disclaimer.

[21] Appl. No.: 08/474,190

[22] Filed: Jun. 7, 1995

Related U.S. Application Data

[62] Division of application No. 08/070,446, filed as application No. PCT/FR92/00955, Oct. 9, 1992, abandoned.

[30] Foreign Application Priority Data

Oct. 10, 1991 [FR] France ................... 91 12478

[51] Int. Cl.$^6$ ............ A61K 39/00; A61K 39/102; C07K 1/00; C07K 14/00
[52] U.S. Cl. .................. 424/184.1; 424/237.1; 424/194.1; 424/193.1; 424/197.11; 424/244.1; 424/240.1; 424/831; 424/236.1; 424/243.1; 424/249.1; 424/250.1; 424/256.1; 424/257.1; 424/258.1; 424/259.1; 424/260.1; 530/402; 530/403; 530/395; 514/2; 514/8; 514/12
[58] Field of Search ............ 424/184.1, 237.1, 424/194.1, 193.1, 197.11, 244.1, 240.1, 831, 236.1, 243.1, 249.1, 250.1, 256.1–260.1; 530/402, 403, 395; 514/2, 12, 8

[56] References Cited

U.S. PATENT DOCUMENTS

| | | |
|---|---|---|
| 4,356,170 | 10/1982 | Jennings et al. . |
| 4,663,160 | 5/1987 | Tsay . |
| 4,673,574 | 6/1987 | Anderson . |
| 4,711,779 | 12/1987 | Porro et al. . |
| 4,727,136 | 2/1988 | Jennings et al. . |
| 4,762,713 | 8/1988 | Anderson . |
| 4,808,700 | 2/1989 | Anderson . |
| 5,122,450 | 6/1992 | Feizi et al. . |
| 5,153,312 | 10/1992 | Porro et al. . |
| 5,204,098 | 4/1993 | Szu et al. . |
| 5,302,386 | 4/1994 | Kasper et al. . |
| 5,306,492 | 4/1994 | Porro et al. . |
| 5,370,872 | 12/1994 | Cryz et al. . |
| 5,445,817 | 8/1995 | Schneerson et al. . |
| 5,476,929 | 12/1995 | Briles et al. . |

FOREIGN PATENT DOCUMENTS

| | | |
|---|---|---|
| 86186 | 8/1983 | European Pat. Off. . |
| 0097407 | 1/1984 | European Pat. Off. . |
| 161188 | 11/1985 | European Pat. Off. . |
| 208375 | 1/1987 | European Pat. Off. . |
| 0245045 | 11/1987 | European Pat. Off. . |
| 86/06729 | of 0000 | WIPO . |
| 87/06267 | of 0000 | WIPO . |
| 9404195 | 3/1994 | WIPO . |

OTHER PUBLICATIONS

Uchida et al, "Oxidative depolymerisation of polymerisation of polysaccharides induced by the ascorbic acid–copper ion systems", Agricultural and Biological Chemistry, vol. 50, No. 10, 1986. pp. 2579–2583.
Paoletti et al, "An oligosaccharide–tetanus toxoid conjugate vaccine against type iii group b streptococcus", Journal of Biological Chemistry, vol. 265, No. 30, 1990, pp. 18278–18283.
Szu et al, "Ultrasonic irradiation of bacterial polysaccharides, characterization of the depolymerized products and some applications of the process", Carbohydrate Research, vol. 152, 1986, pp. 7–20.
Hayes, Science 260:1279–1286 (1993).
Fox,Bio/Technology 12:128 (1994).
Porro et al., Medicine Tropicals, 43(2), 129 (1983).
Porro et al., Molecular Immunology , 22(8), 907 (1985).
Meikle and Bundle, Glycoconjugate J., 7, 207 (1990).
Edelman et al. 1990. Int. Rev. Immunol. 7:51–66.
Schneerson et al. 1992. Inf & Imm. 60(9):3528–3532.
Cryz et al. 1990. Inf & Imm 58(2):373–377.
Langer 1990. Science 249:1528–1533.
Anderson et al. 1985 J. Clin. Invest. 76:52–59.
Munson 1990. Can. J. Vet. Res. 54:563–567.
Lee et al. 1994. Vaccine 12(10): 875–878.
Fattom et al. 1990. Inf & Imm. 58(7):2367–2374.
Aron et al. 1993. J. Clin. Microbiol. 31(4):975–978.
Schneerson et al. 1980 J. Exp. Med. 152:361–376.
Jennings 1992 J. Inf. Dis. 165(Supp4):S156–S159.
Szu et al. 1989 Inf. & Imm. 57(12):3823–3827.
Szu et al 1987 J. Exp. Med. 166:1510–1524.
Sarvas et al. 1988. Scand. J. Immunol. 28:471–79.

*Primary Examiner*—Nita Minnifield
*Attorney, Agent, or Firm*—Nixon & Vanderhye, P.C.

[57] ABSTRACT

An oligoside derived from an antigen polyoside obtained from a pathogenic agent, a method for its preparation, and its use particularly as a vaccinal agent. The oligoside is prepared by oxidation-reduction depolymerisation reaction.

65 Claims, 5 Drawing Sheets

OLIGOSACCHARIDE DERIVED FROM AN ANTIGENIC POLYSACCHARIDE OBTAINED FROM A PATHOGENIC AGENT

This is a division of application Ser. No. 08/070,446, filed Oct. 7, 1993 now abandoned, and is based on and claims priority of PCT/FR92/00955, filed Oct. 9, 1992, and FR 9112478, filed Oct. 10, 1991.

The subject of the present invention is an oligosaccharide derived from an antigenic polysaccharide obtained from a pathogenic agent, a process for preparing it and its use especially as vaccinal agent.

Bacteria as well as fungi such as yeasts incorporate polysaccharides into their surface structure. Thus a large majority of bacteria are covered with an exudate of polysaccharide nature which is bound to the bacterium more or less strongly but which is not strictly speaking an envelope. This exudate is called capsule or glycocalyx. Moreover, the outer membrane of Gram-negative bacteria consists, inter alia, of lipopolysaccharide (LPS). Finally, polysaccharides also occur in the wall of fungi. These polysaccharides are in fact surface antigens which induce an immunological response in an infected mammal.

Such polysaccharides are formed on the basis of repeating units in which the constituents and the bonds are defined and which are each characteristics of the fungal or bacterial species considered. These repeating units contain the epitopes, the antigenicity-determining structures. By way of illustration, various types of repeating units obtained from capsular polysaccharides or from lipopolysaccharides are presented in FIG. 1. The repeating units often contain very labile functional groups such as for example phosphate functional groups which are present in the skeleton of the molecule or in a branched position as well as for example O-acetyl and pyruvate groups.

A polysaccharide in fact consists of a combination of polymeric molecules containing glycoside units in an amount which may vary from one molecule to another. Consequently, a polysaccharide can be described in terms of molecular weight only by a mean molecular weight. In the case of a homopolysaccharide, the glycoside units are monosaccharides. In the case of a heteropolysaccharide, the glycoside units form a chain of constituents linked to each other in a defined manner.

Regarding the mean molecular weight of a polysaccharide, it can be assessed by gel filtration. In this case, the molecular weight is expressed in terms of elution constant ($K_D$) or dextran equivalent (DEq) according to the method described by Granath et al., J. Chrom. (1967) 28: 69, which can be summarised as follows;

A polysaccharide solution is analysed on an exclusion-diffusion gel chromatography column which separates elements according to their molecular weight. This type of gel is commercially available, for example under the trade names of Sephadex (Pharmacia), Bio-Gel (Bio-Rad), Fractogel (Toyo-Soda), Sepharose (Pharmacia), and Sephacryl (Pharmacia). The zone of fractionation of the gel should obviously be adapted to the range of molecular weights represented within the molecular population to be analysed. By way of example, it can be stated that the gel filtration columns Sepharose 2BCL, 4BCL and 6BCL have a zone of fractionation, determined in dextran equivalent, of 20,000,000 to 100,000; 5,000,000 to 20,000 and 1,000,000 to 10,000 respectively. Generally, a salt solution, for example 0.2 M sodium chloride, is used as eluent. An elution constant is calculated based on the following formula:

$$\frac{Ve - Vo}{Vt - Vo}$$

Ve is the elution volume of the preparation considered; Vt is the total volume of the column; and Vo is the dead volume of the column.

Figure 1A:
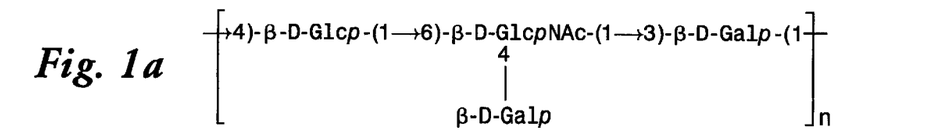
FIG. 1 represents the formulae of the repeating units of the capsular polysaccharide of S. pneumoniae type 14 (a), type 1 (b), of S. typhi (c), of S. pneumoniae type 6B (d), of H. influenzae type B (e), of S. pneumoniae type 19F (f), of N. meningitidis group A (g), of S. pneumoniae type 18C (h), type 23F (i), of Klebsiella ozaenae serotype K4 (j), of Shigella flexneri serotype 1b (k) and Cryptococcus neoformans strain 98 (l). It can be observed that (a) corresponds to a neutral polysaccharide, that (b) and (c) correspond to polysaccharides containing uronic acids in the polysaccharide chain, that (d) to (i) correspond to phosphorylated polysaccharides, that (j) and (k) correspond to lipopolysaccharides which are anionic and neutral respectively and that (l) corresponds to an anionic fungal polysaccharide.
Figure 1B:
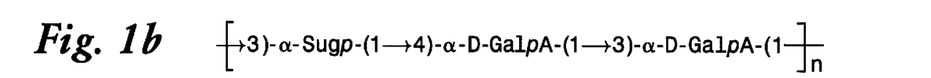
Figure 1C:
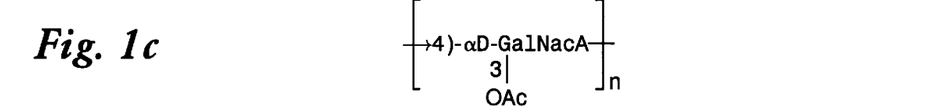
Figure 1D:
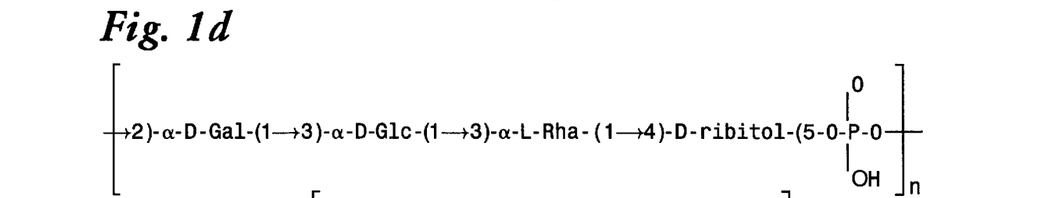
Figure 1F:
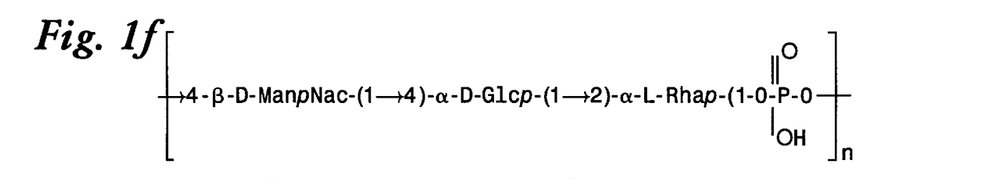
Figure 1G:
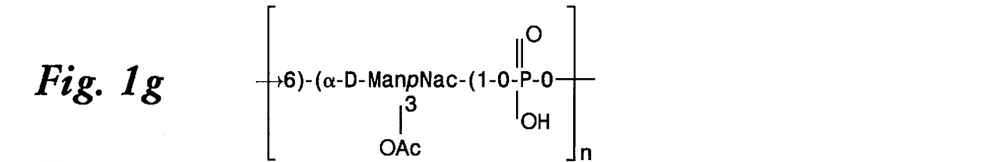
Figure 1H:
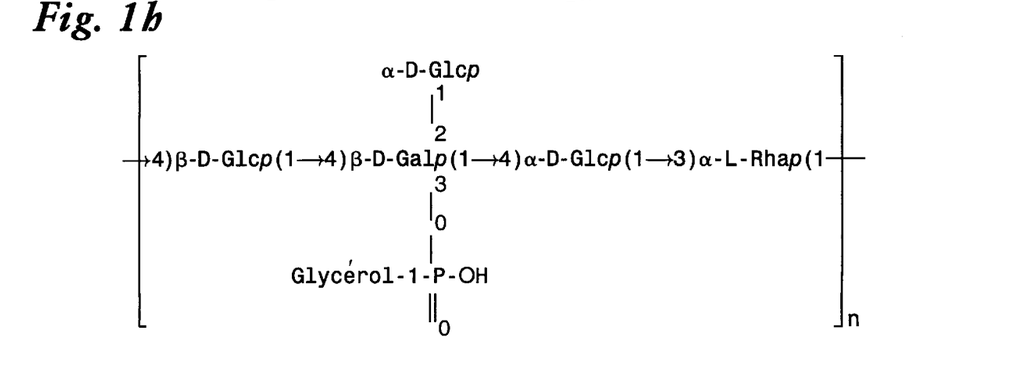
Figure 1I:
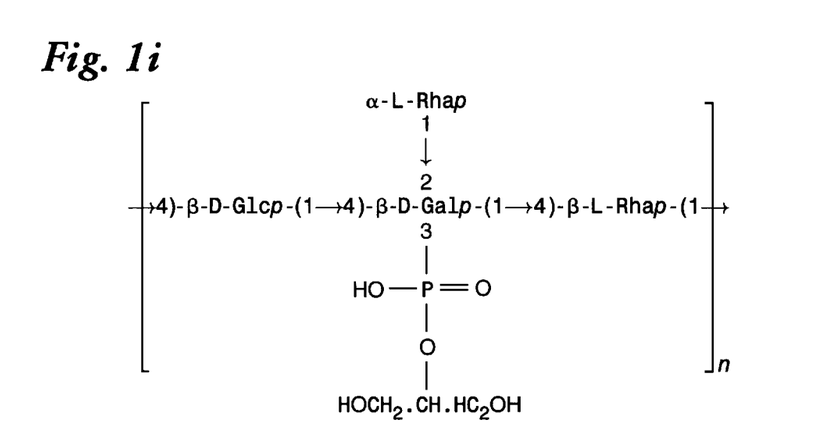
Figure 1J:
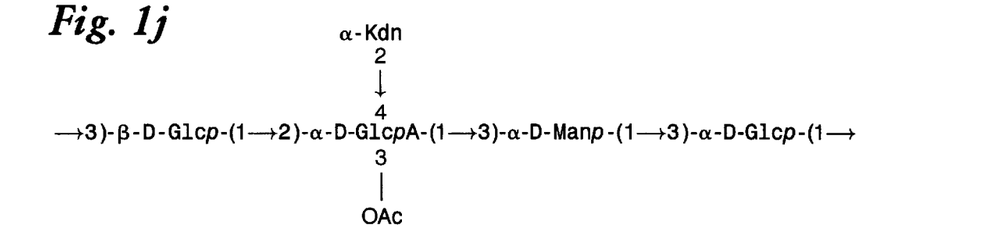
Figure 1K:
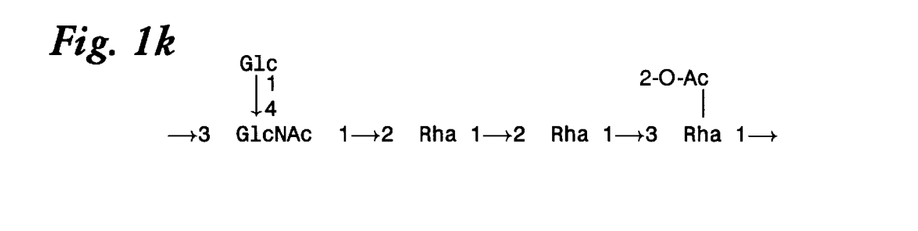
Figure 1L:
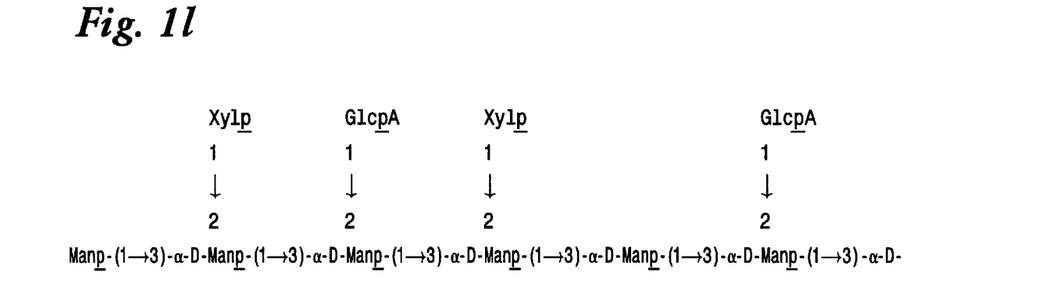
Figure 2A:
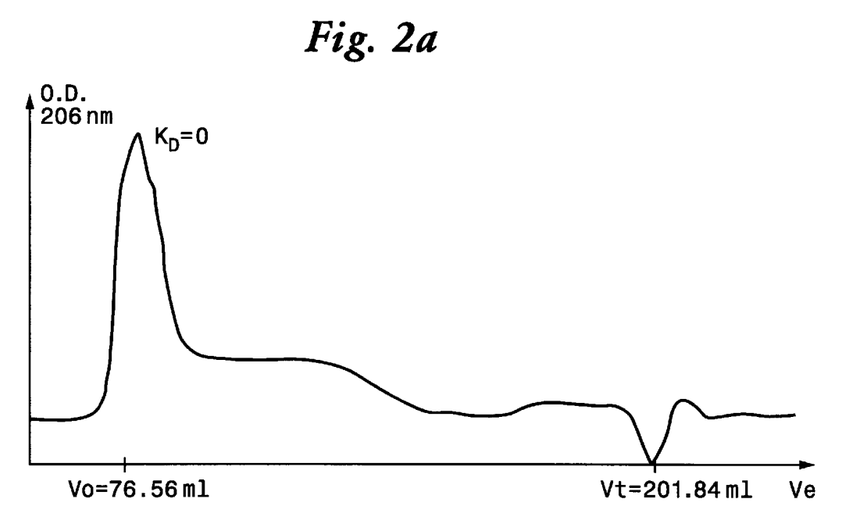
FIGS. 2a and 2b represent the elution profiles of the nonfragmented polysaccharides of S. typhi (2a) and of S. pneumoniae type 1 (2b) on a Sepharose 4BCL column. The conditions for chromatography are as follows: 2 ml of a polysaccharide solution at 5 mg/ml are loaded on the Sepharose column equilibrated beforehand with 0.2 M NaCl. The elution is performed with 0.2 M NaCl at a rate of 42 ml/h. The elution profile is automatically analysed by measuring the optical density at 206 nm. In 2a and 2b, the dead volume of the column is 76.56 ml while the total volume is 201.84 ml.
Figure 2B:
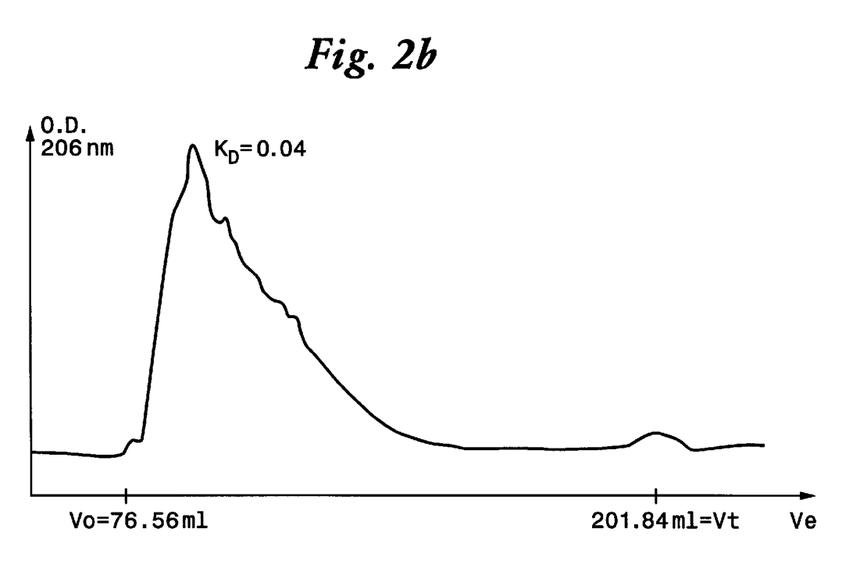

By way of example, FIGS. 2a and 2b present the respective elution profiles of the polysaccharides of *Salmonella typhi* and of *Streptococcus pneumoniae* type 1 on a Sepharose 4BCL column. The polysaccharide of *S. typhi* is therefore composed of polymers in which the highest molecular weights are not assessable on Sepharose 4BCL. Likewise, the polysaccharide of *S. pneumoniae* type 1 is essentially composed of polymers whose molecular weights vary from a $K_D$ of zero to 0.45. By definition, the mean elution constant of the polysaccharide is assessed at the point of intersection of the tangents of the slopes of the elution profile; or roughly, at the peak of the elution profile. Thus, the mean elution constant of the polysaccharides presented in FIGS. 2a and 2b is zero and 0.04 respectively.

Figure 3:
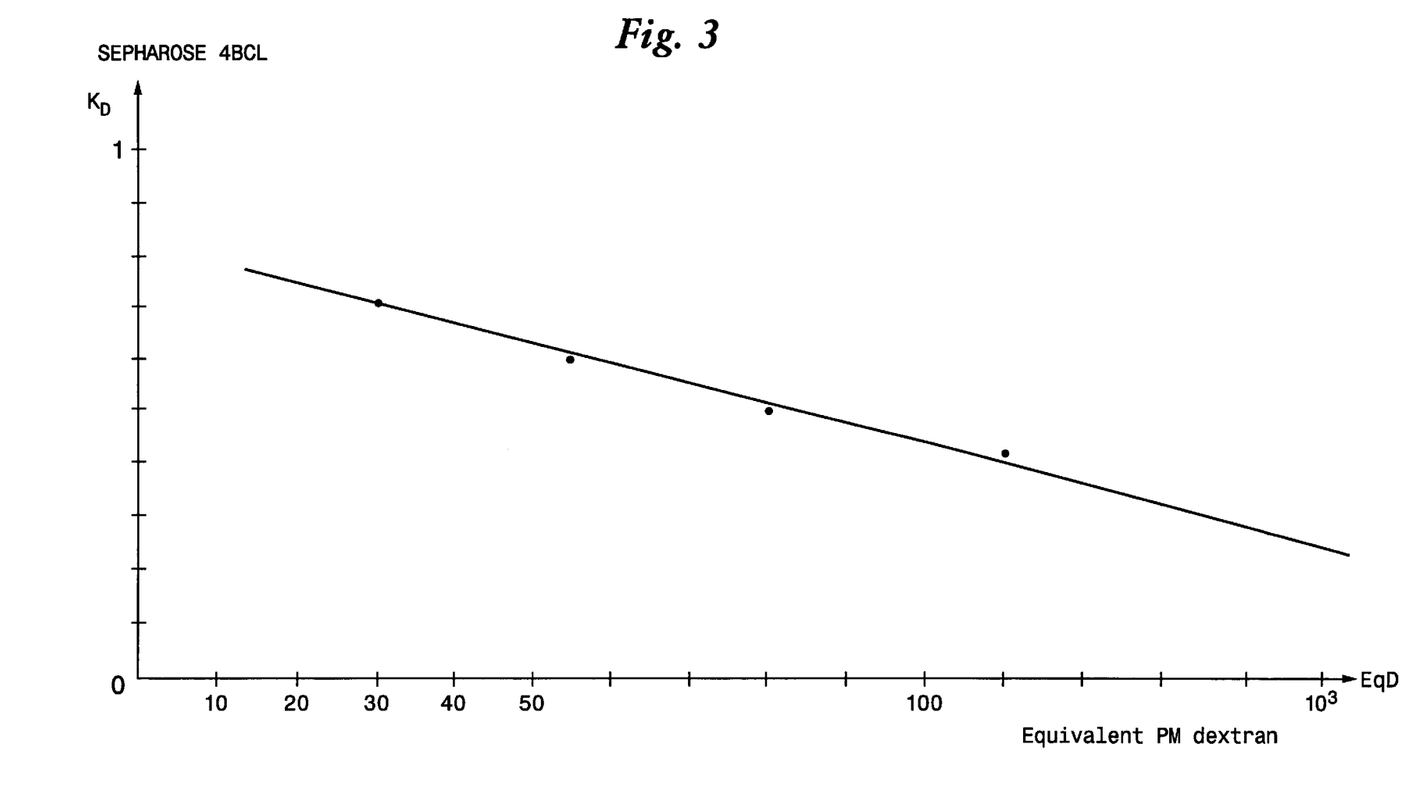
FIG. 3 represents a calibration series for dextran from 500,000 to 20,000.

On the basis of a calibration series prepared using dextran, an elution constant can be converted to molecular weight expressed in DEq. By way of example, FIG. 3 presents an example of a calibration series.

Because of their antigenicity, polysaccharides, which are surface antigens of pathogenic agents, eg. bacteria or fungi, are good candidates as vaccinal agent. Vaccines comprising a polysaccharide extract have indeed proved effective in adults. However, this is not the case in young children. In order to overcome this major problem, it was successfully proposed to covalently link the polysaccharides to proteins, thereby conferring on the molecules thus obtained a T-dependent character and increasing their immunogenicity.

Among the vaccines based on polysaccharides, there are so far vaccines against infections caused by *Neisseria meningitidis* group A, C, Y or W 135, by *Streptococcus pneumoniae*, by *Haemophilus influenzae* type B and by *Salmonella typhi*.

Although the antigenic polysaccharides of pathogenic agents are potentially advantageous as immunogens, their use is difficult because of their high mean molecular weight which may be as high as several million dextran equivalents. In particular, when it is desired to use the polysaccharide in the form of a conjugate, that is to say coupled with a protein, technical problems are encountered which are difficult to resolve. During the coupling process, a gel or a flocculant material may form, thus rendering the conjugate difficult to sterilise by filtration.

To overcome this obstacle, it has already been proposed to reduce the size of the polysaccharides in order to make them easier to handle. Various cleavage methods have been proposed for this purpose. Thus, they are for example well established methods such as fragmentation by ultrasound or by alkaline hydrolysis in acidic, basic or enzymatic medium. However, these fragmentation methods are far from satisfactory. Indeed, too often they result in total or partial destruction of the characteristic epitopes by the loss of chemical functional groups essential for the antigenic specificity.

Thus, acid or alkaline hydrolysis of the capsular polysaccharide of *S. typhi* or of *N. meningitidis* group A removes the acetyl groups which are required for the antigenic specificity of the polysaccharide. Furthermore, the correct reacetylation of the fragments obtained by alkaline hydrolysis is very difficult if not impossible.

Moreover, with the method of fragmentation by alkaline hydrolysis, it is not always possible to obtain fragments of relatively homogeneous size, whereas pharmaceutical practice requires homogeneous products, of constant and standardised quality.

In the case of fragmentation by ultrasound, it has for example been shown that the terminal phosphate groups of the polysaccharide of *H. influenzae* type B are lost by ultrasound treatment. This may lead to a fear that phosphate groups in the branched position on the polysaccharide chains are likewise removed during such a treatment.

Moreover, although fragments of relatively homogeneous size can be obtained using ultrasound, the production of fragments of sufficiently small size by the ultrasound method requires a very long treatment time which may cause, among other disadvantages, a rapid deterioration of the equipment. Its efficiency being limited, the application of ultrasound on an industrial scale is to be excluded.

Finally, the use of enzymatic depolymerisation of polysaccharides is limited to the polysaccharides for which appropriate enzymes are known. This major disadvantage is however inherent in the highly specific nature of enzymes towards their substrate.

For the vaccinal domain, a significant technical and economic advance would therefore be to be able to have a depolymerisation process which no longer exhibits the various disadvantages of the processes of the state of the art. In other words, it is necessary in particular to be able to have a process for the depolymerisation of antigenic polysaccharides which has a combination of advantageous properties because:

It makes it possible to obtain oligosaccharides having a reduced number of glycoside units while preserving the essential structural determinants of at least one epitope of the polysaccharide to be fragmented.

It is possible to use it for any antigenic polysaccharide structure envisaged.

It makes it possible to obtain fragments of sufficiently homogeneous size, and

It is low in cost and extremely simple to use.

Surprisingly, it has now been found that these objectives are achieved by an oxidation-reduction depolymerisation reaction.

Up until now, such a method, often designated in English by the abbreviation ORD, was used to fragment polysaccharides such as heparin, hyaluronic acid, dextran and DNA and this for completely different purposes from those pursued by the present application. The aim was for example to reduce the viscosity of the products or, in the case of a linear molecule such as heparin, to obtain fragments of reduced size which were known to have a different anticoagulant activity. Of course, since the products to which this method was applied were not of immunogenic importance, a study of the integrity of the repeating units of the fragments obtained was not undertaken.

Moreover, there are numerous prior publications such as for example K. Uchida, Carbohydrate Research, (1988) 173: 89–99; H. Uchiyama, Journal of Biological Chemistry, (1990) 265: 7753–7759; S. W. Green, The Carbohydrates Chemistry and Biochemistry IB; Academic Press (1980): 1132; A. Herp, The Carbohydrates Chemistry and Biochemistry IB; Academic Press (1980): 1276; Kochetkov et al, Radiation Chemistry of Carbohydrates, Pergammon Press, Oxford, (1979) which describe the ORD reaction as destructive either of the phosphate groups or of the carbohydrate rings by cleavage of the carbon—carbon bonds of the ring.

The overall impression which emerged from the prior state of the art has meant that the ORD reaction is generally recognised as destructive.

There was therefore nothing to suggest that ORD might be better than for example the method using alkaline hydrolysis or using ultrasound treatment for the desired objectives, i.e. the preservation of the epitopes.

Accordingly, before the present invention, it had never been demonstrated that it was possible to obtain oligosaccharides, whose characteristic repeating unit structure is preserved, by oxidation-reduction fragmentation of the respective polysaccharides so as to be able to use them as active agent in formulations which make it possible to reinforce the immune defences of an individual.

It has now been discovered that it is possible to use the ORD method to obtain oligosaccharides which have preserved at least one antigenic determinant of the starting polysaccharide.

Furthermore, it was also observed that the oxidation-reduction depolymerisation method when applied to an antigenic polysaccharide made it possible to obtain, under favourable conditions, fragments which were completely satisfactory from the point of view of homogeneity of size in spite of the fact that it is known that the ORD reaction is a free radical-producing reaction which cleaves the polysaccharide in a random manner.

Consequently, the invention provides an oligosaccharide which has preserved at least one antigenic determinant of an antigenic polysaccharide obtained from a pathogenic agent, characterised in that it is prepared by a process comprising the steps consisting in (i) subjecting the said polysaccharide to an oxidation-reduction depolymerisation reaction, (ii) recovering the oligosaccharide thus obtained and, if desired, (iii) coupling it with a conjugation partner or with a carrier in order to obtain the said oligosaccharide in the form of a conjugate or bound to a carrier.

"Oligosaccharide" is understood to mean a combination of molecules; each molecule having a reduced number of glycoside units relative to the starting polysaccharide and containing for example from 4 to 500 glycoside units.

The mean molecular weight of an oligosaccharide is defined according to the rules explained above for a polysaccharide. Generally, an oligosaccharide according to the invention may have a mean elution constant on a Sepharose 4BCL column of 0.2 to 1, alternatively of 0.3 to 0.9 in particular of 0.4 to 0.8, for example of 0.6 to 0.7. In other words, such an oligosaccharide has a mean molecular weight of 200,000 to 2,000 DEq, especially of 150,000 to 10,000 DEq, in particular of 60,000 to 30,000 DEq.

According to a preferred aspect of the present invention, the antigenic polysaccharide is a surface antigen obtained from a pathogenic agent which may be a fungus as well as a Gram-negative or Gram-positive bacterium, especially of the genus Staphylococcus, Streptococcus, Klebsiella, Salmonella, Escherichia, Neisseria, Shigella or Haemophilus.

The bacterial pathogenic agent is for example *Streptococcus pneumoniae, Neisseria meningitidis, Salmonella typhi* or *Haemophilus influenzae*.

The fungal pathogenic agent may be a yeast, more particularly selected from the genera Candida, Cryptococcus, Hansenula, Lipomyces, Rhinocladiella and Rhodotorula.

For the purposes of the present invention, an oxidation-reduction reaction is carried out in the presence of at least one oxidation-reduction system which may be especially chosen from thiols, e.g. glutathion, cysteine; oxygen; hydroquinone; ions of multivalent metals, e.g. iron and copper; ascorbic acid, hydrogen peroxide; these last two being preferred.

The different experimental parameters which can influence the kinetics of the reaction (product concentration, pH, temperature, reaction time) can be easily determined by persons skilled in the art according to the characteristics of the starting polysaccharide, the oxidation-reduction system chosen and the mean size of the fragments which it is desired to obtain. When these fragments are intended especially for vaccinal purposes, persons skilled in the art will in particular take care to adjust the different parameters so as to obtain fragments of a suitable mean size, that is to say which preserve a good antigenicity and adapted, where appropriate, to the use of conjugates; for example, of an order of magnitude as defined above. Generally, the optimal reaction conditions may be determined during routine tests. As a guide, experimental values which make it possible to obtain good results are however specified in the examples below.

A polysaccharide intended to be subjected to a process according to the invention may be extracted and purified according to known methods, in particular by precipitation with alcohol or with cetyltrimethylammonium bromide or by gel filtration. For a review of these methods, reference can be made in particular to R. I. Whistler, in Methods in Carbohydrate Chemistry, (1965) I: 3–62.

The polysaccharide is advantageously prepared in aqueous solution at a concentration of 5 mg/ml. It is indicated that an advantageous concentration may vary from 0.5 to 50 mg/ml, in particular from 0.5 to 10 mg/ml. Such an aqueous solution can be used as starting material.

An oxidation-reduction system as defined above is added to the polysaccharide preparation all at once or in a continuous or discontinuous manner in a final oxidation-reduction system:polysaccharide weight ratio which may vary especially from 0.01 to 10, in particular from 0.1 to 5, for example from 0.1 to 1.

A process according to the invention can be used at a pH of 3 to 8.5, in particular of 3 to 6.5. Likewise, the temperature of the reaction medium is not critical; it may especially vary from 4 to 60° C., in particular from 18 to 40° C.

The time required to achieve a desired fragmentation of the polysaccharide is generally from 30 min to 1 h except in special cases; for example for the polysaccharide Vi of S. typhi, the reaction time is substantially longer. The reaction time can be adjusted as a function of the size of the fragments which it is desired to obtain.

According to a specific embodiment, to an aqueous preparation of a polysaccharide having a concentration of 0.5 to 50 mg/ml, in particular of 0.5 to 10 mg/ml, is added ascorbic acid up to a final concentration of 0.01 to 25 mg/ml, in particular of 0.1 to 10 mg/ml. The oxygen naturally dissolved in the reaction medium is generally sufficient; if this was not the case, more of it could be injected into the medium. In order to accelerate the reaction, the procedure is preferably carried out in the presence of a soluble salt of a metal with several oxidation states, such as iron or copper. The metal salt(s) may be added to a concentration of 1 $\mu$M to 100 mM, in particular of 1 to 10 mM.

According to an alternative embodiment to that set forth above, ascorbic acid is replaced with hydrogen peroxide which may be added up to a concentration of 0.1 to 100 mM, in particular of 0.5 to 10 mM, optionally in the presence of a metal salt.

An oligosaccharide prepared by subjecting a polysaccharide to an ORD depolymerisation reaction consists of a combination of molecules whose mean elution constant is less than that of the polysaccharide from which it is derived by fragmentation (the comparison quite obviously being made using the same chromatographic column). The oligosaccharide can be isolated using a conventional technique, for example by precipitation by means of an appropriate precipitating agent, e.g. acetone or alcohol, by filtration on a membrane having an appropriate separation threshold, by exclusion-diffusion or ion-exchange chromatography. Subsequently, the choice can be made to use only certain oligosaccharide fractions containing molecules having an elution constant equal to, or in the vicinity of, the mean elution constant.

Optionally, the oligosaccharide according to the invention may be coupled, via covalent bonding, with a compound of peptide or protein nature or with another organic polymer such as for example polyacrylate in order to form a conjugate capable of promoting the immunogenicity of the oligosaccharide especially in a mammal. The partner for conjugation may be especially a bacterial protein, for example a toxin, the corresponding anatoxin or a subunit of a multimeric toxin as well as a membrane protein, a subunit of a multimeric membrane protein or a cytoplasmic protein. By way of example, there may be mentioned Pertussis toxin, cholera toxin, tetanus toxin and diphtheria toxin. These proteins can be extracted from the original bacteria or alternatively can be obtained by the recombinant route.

A reaction for coupling, via covalent bonding, an oligosaccharide with a conjugation partner so as to obtain a conjugate which can be used as a vaccine, can be used in a conventional manner. For example a functional group can be created on the oligosaccharide which is capable of reacting with a functional group of the conjugation partner. A bifunctional coupling agent can also be reacted with the oligosaccharide and then with a conjugation partner, or vice versa. For a review of these various coupling methods, reference can be made in particular to W. E. Dick and M. Beurret in Conjugates Vaccines, J. M. Cruse, R. E. Lewis Jr Eds, Contrib. Microbiol. Immunol. Basel, Karger (1989) 10: 48. Furthermore, the oxidation-reduction fragmentation process introduces reducing groups, especially into the oligosaccharide derived from the polysaccharides of S. pneumoniae type 6B and 19F, H. influenzae and N. meningitidis group A. This therefore makes it possible to use the reductive amination conjugation technique.

The immunogenicity of an oligosaccharide according to the invention may also be enhanced using carrier liposomes to which the oligosaccharides are covalently bound. Immunogenicity is also enhanced by vectors which retain the oligosaccharide by incorporation by means of ionic or hydrophobic forces, such as, for example, cyclodextrins, liposomes and ISCOMS.

The invention therefore relates to an oligosaccharide as defined above, provided in various forms, in particular in the form of a conjugate or coupled with a carrier liposome, or incorporated into a vector. According to a preferred aspect of the present invention, the oligosaccharide is in the form of a conjugate.

An oligosaccharide according to the invention is especially useful for reinforcing the immune defences of an individual, in mammals and especially in humans, for example to prevent or attenuate the effects of an infection induced by a pathogenic agent, e.g. a bacterial infection or a mycosis. The mixtures of oligosaccharides according to the invention which are derived from different antigenic polysaccharides, as well as the mixtures of an oligosaccharide according to the invention with active ingredients other than an oligosaccharide according to the invention, are also useful. Such mixtures are suitable for the preparation of polyvalent vaccines.

Consequently, the invention also provides:

A pharmaceutical composition which comprises as active ingredient at least one oligosaccharide according to the invention; the composition is especially a vaccine;

The therapeutic use of an oligosaccharide according to the invention;

A method, e.g. of vaccination, for reinforcing the immune defences of an individual, which comprises the act of administering, in sufficient quantity from the therapeutic point of view, at least one oligosaccharide according to the invention to a subject requiring such a treatment, e.g. such a vaccination;

The use of an oligosaccharide according to the invention as active ingredient in the preparation of a pharmaceutical composition intended to reinforce the immune defences of an individual;

A process for the preparation of a pharmaceutical composition as defined above, characterised by the fact that (i) the starting polysaccharide is subjected to an oxidation-reduction depolymerisation reaction, (ii) if desired, either the oligosaccharide obtained is coupled with a conjugation partner or a liposome, or it is incorporated into liposomes, ISCOMS or cyclodextrins, and (iii) the product obtained is made into an appropriate pharmaceutical form.

A preferred pharmaceutical composition comprises at least one oligosaccharide in the form of a conjugate.

The pharmaceutical composition according to the invention may be manufactured in a conventional manner. In particular, an oligosaccharide according to the invention is combined with a pharmaceutically acceptable diluent or carrier, for example a pyrogen-free physiological saline solution. In addition, a composition according to the invention may contain the customary ingredients such as a buffer, a preserving or stabilising agent, an adjuvant and, where appropriate, a freeze-drying excipient. An oligosaccharide according to the invention may be preserved in the presence of a diluent, a carrier or an ingredient as mentioned above. Alternatively, a diluent, a carrier or an ingredient may be added just before use.

Accordingly, the invention alternatively provides a kit containing:

a) a pharmaceutical composition essentially consisting of at least one oligosaccharide according to the invention as active ingredient;

b) a composition comprising at least one element selected from a pharmaceutically acceptable diluent or carrier, a compound with buffering power, a preserving or stabilising agent and an adjuvant;

c) instructions for the concomitant administration, e.g. in the form of a mixture, of the compositions described under a) and b).

A composition according to the invention may be administered by any conventional route, in particular subcutaneously, intramuscularly or intravenously, for example in the form of an injectable suspension, or orally. The administration can be carried out in a single dose or repeated once or several times after a certain interval of time. The appropriate dosage varies according to various parameters, for example, the individual treated or the mode of administration. It is indicated, however, that good results can be obtained with a unit dose of 1 to 200 µg of oligosaccharide in a volume of about 0.5 ml.

The invention is presented in greater detail in the following examples and with reference to FIGS. 1 to 4.

EXAMPLE 1

Fragmentation of the Polysaccharide Vi of S. typhi in the Presence of Ascorbic Acid A dry powder of the polysaccharide Vi, obtained according to the method of Gotschlich et al., Prog. Immunobiol. Standard. (1972) 5: 485 is taken up in pyrogen-free water in an amount of 1 mg/ml. The mean molecular weight (MW) of the polysaccharide corresponds to a $K_D$ of zero on a Sepharose 4BCL column.

To 500 ml of this preparation, preheated to 37° C., are slowly added, continuously for 2 h, 12.5 ml of an aqueous solution containing 100 mM ascorbic acid, 10 mM $CUSO_4$ and 10 mM of $FeSO_4$, equivalent to a final ascorbic acid concentration of 0.44 mg/ml. The pH of the reaction medium thus obtained is about pH 4. The reaction is continued with gentle stirring for about 3 h (including reagent addition time) at 37° C.

The reaction mixture is then filtered on a 3K ultrafiltration membrane (cut-off: 3 kilodaltons). The retentate is washed once with a 0.5 M NaCl solution, then a second time with water. The retentate is taken up in about 100 ml of water and then freeze-dried for preservation.

Figure 4A:
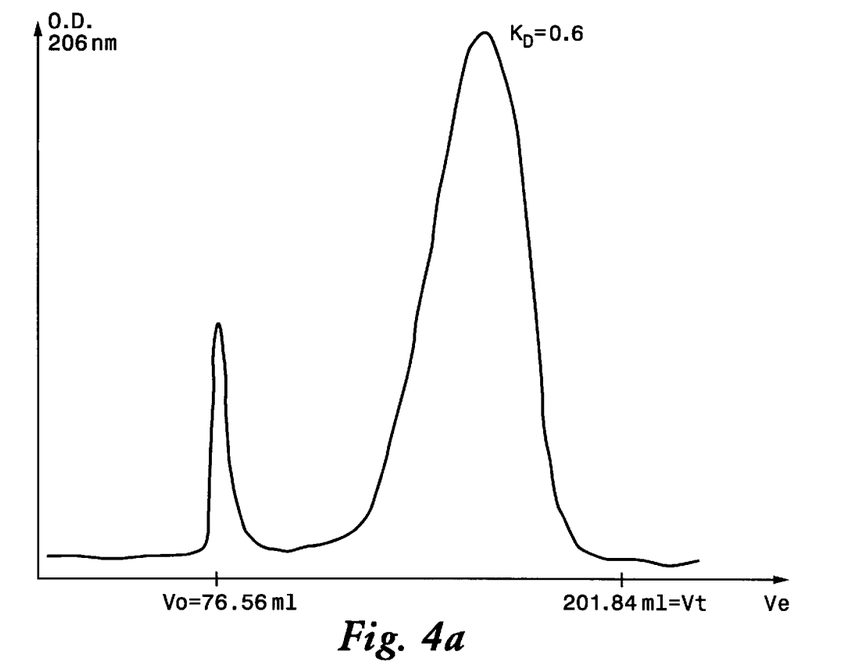
FIGS. 4a and 4b represent the elution profiles of oligosaccharides obtained by oxidation-reduction fragmentation of the polysaccharides of S. typhi (4a) and of S. pneumoniae type 1 (4b) on a Sepharose 4BCL column. The conditions for chromatography are as previously outlined in the description of FIG. 2.
Figure 4B:
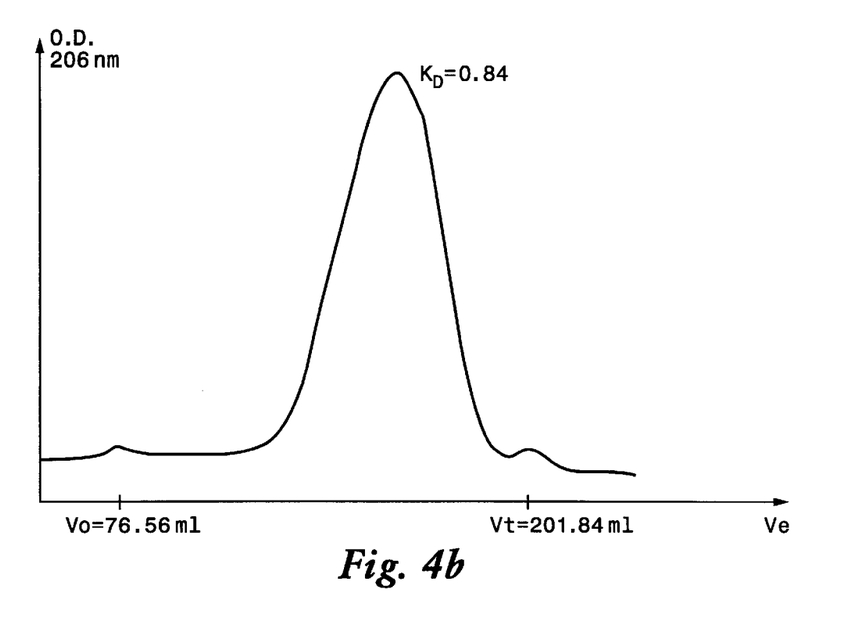

The level of cleavage is of the order of 95%, as calculated by integration of the curves obtained by filtration on Sepharose 4BCL gel (FIG. 4a). Moreover, the mean MW of the oligosaccharide thus obtained is estimated by the method of Granath et al. (supra). The latter, expressed as mean elution constant, is of the order of 0.6, equivalent to a MW of 60,000 DEq (taking dextran as reference).

Analysis of the oligosaccharide by NMR (nuclear magnetic resonance) spectrometry clearly indicates that the structure of the repeating unit characteristic of the polysaccharide was preserved after fragmentation. In particular, there was no loss of branched functional groups or of sugars from the polysaccharide skeleton.

The chemical functional groups characteristic of the repeating unit of the polysaccharide Vi are analysed by colorimetric assay. The O-acetyl group in a branched position is assayed by the method of Hestrin, Biol. Chem. (1949) 188: 249 while the polyacid of the linear structure is assayed by the method of Stone et al., Clin. J. Microbiol. (1988) 28: 719. The assays are carried out in parallel on the nonfragmented polysaccharide Vi and on the oligosaccharide formed.

The [O-acetyl]/[polyacid] ratios measured for the polysaccharide and the oligosaccharide are identical. This indeed shows that the method of fragmentation of the polysaccharide made it possible to preserve all the labile O-acetyl groups.

EXAMPLE 2

Fragmentation of the Polysaccharide Vi of S. typhi in the Presence of Hydrogen Peroxide ($H_2O_2$)

A dry powder of the polysaccharide Vi obtained according to the method of Gotschlich et al., (supra) is taken up in 0.2 M phosphate buffer, pH 7.5, in an amount of 0.4 mg/ml. The MW of the polysaccharide corresponds to a $K_D$ of zero on a Sepharose 4BCL column.

To 100 ml of this preparation, preheated to 37° C., are added slowly, with gentle stirring, 11 ml of an aqueous solution containing 0.3 mg/ml of $H_2O_2$ and 1.1 ml of a $CUSO_4$ solution at 2.6 mg/ml. The reaction is continued with gentle stirring for about 1 h at 37° C.

The experiment is repeated under the same conditions except for the reaction time which is 2 hours instead of one.

In both cases, each oligosaccharide thus obtained is then recovered and purified as described in Example 1.

Likewise, the characteristics of the oligosaccharides thus obtained are determined according to the methods mentioned in Example 1. The results are as follows:

In both cases, the level of cleavage of the polysaccharide Vi is of the order of 100%.

The mean MW of the oligosaccharides formed after one and two hours corresponds to a $K_D$ of the order of 0.7 and 0.8 respectively; equivalent to 30,000 and 10,000 DEq.

In both cases, no modification is observed in the structure of the repeating unit.

EXAMPLE 3

Fragmentation of the Polysaccharide of N. meningitidis Group A

A dry powder of the polysaccharide of N. meningitidis group A as obtained by the method of Gotschlich et al. (supra) is taken up in 0.2 M phosphate buffer, pH 7.5, either in an amount of 1 mg/ml or in an amount of 5 mg/ml. The mean MW of the polysaccharide corresponds to a $K_D$ of 0.15 as measured on a Sepharose 4BCL column.

The preparations at 1 and 5 mg/ml are preheated to 37° C.

3a) To 100 ml of the preparation at 1 mg/ml, is added 0.75 ml of a reaction solution containing 100 mM ascorbic acid, 10 mM $CUSO_4$ and 10 mM $FeSO_4$. The reaction is continued with stirring for 1 h 30 min at 37° C. Then 0.75 ml of the reaction solution is again added; a final ascorbic acid concentration of 0.26 mg/ml is thus obtained. The reaction is again continued for 1 h 30 min under the same conditions.

3b) To 100 ml of the preparation at 5 mg/ml, are added 1.5 ml of reaction solution containing 100 mM ascorbic acid, 10 mM $CUSO_4$ and 10 mM $FeSO_4$, equivalent to a final ascorbic acid concentration of 0.26 mg/ml. The reaction is continued with stirring for 1 h 30 min at 37° C.

The oligosaccharides obtained in 3a) and 3b) are recovered and purified as described in Example 1. Likewise, the analyses are carried out as mentioned in Example 1. In both cases, a 100% cleavage level is observed without deterioration of the structure of the repeating unit as analysed by NMR. The mean MW of the oligosaccharide obtained in 3a) corresponds to a $K_D$ of 0.7 (equivalent to 30,000 DEq) while the mean MW of the oligosaccharide obtained in 3b) corresponds to a $K_D$ of the order of 0.4 (equivalent to 110,000 DEq).

These results as whole indicate that by varying the experimental conditions (polysaccharide and reactive oxidation-reduction agent concentration as well as the mode of addition of the reactive agent and the reaction time), oligosaccharides of substantially different mean MW can be obtained while preserving a 100% cleavage level.

Finally, this example as well as Example 2, indeed show that the fragmentation is by oxidation-reduction and not by acid or alkaline alkaline hydrolysis since this fragmentation can be performed at close to neutral pH.

EXAMPLE 4

Fragmentation of the Polysaccharide of S. pneumoniae Types 1 and 19F and of H. influenzae type B, in Buffered Medium Example 3 (3a and 3b) is repeated using the polysaccharides of S. pneumoniae types 1 and 19F as obtained according to the method described in French Patent Application FR 2,495,939 published on Jun. 18, 1982 as well as the polysaccharide of H. influenzae type B obtained according to the method of Gotschlich et al. (supra);

The results are as follows:

| Strain | Mean MW of the polysaccharide (expressed in $K_D$) | Procedure a) Mean MW of the oligosaccharide | Procedure a) Cleavage level | Procedure b) Mean MW of the oligosaccharide | Procedure b) Cleavage level |
| --- | --- | --- | --- | --- | --- |
| S. pneumoniae 1 | 0.04 | 0.84 | 100 | 0.35 | 100 |
| S. pneumoniae 19F | 0.04 | 0.80 | 100 | 0.38 | 100 |
| H. influenzae B | 0.1 | 0.75 | 100 | ND | ND |

ND: not determined

Analysis of the oligosaccharide by NMR (nuclear magnetic resonance) spectrometry clearly indicates that the structure of the repeating units characteristic of the polysaccharides was preserved after fragmentation.

EXAMPLE 5

Fragmentation of the Polysaccharides of N. meningitidis Group A and of S. pneumoniae Types 1, 14, 18C, 19F and 23F, in Unbuffered Medium The polysaccharide preparations as well as the reactions are carried out as described in Examples 3 and 4, taking the following exceptions into account: (i) the polysaccharide preparations are prepared at 5 mg/ml in pyrogen-free water, (ii) the reaction solution is added all at once to a final concentration of 2.5 mg/ml and (iii) the reaction is continued only for 1 hour.

The oligosaccharides obtained are recovered and purified as described in Example 1. Their characteristics are evaluated as mentioned in Example 1. The cleavage level for each of the polysaccharides is 100% without there being deterioration of the structure of the repeating units. This last point was also demonstrated by colorimetric assay: the hexoses are assayed by the method of Scott et al., Anal. Chem. (1953) 25: 1650, the hexosamines by the method of Gatt et al., Anal. Biochem. (1965) 15: 167, the rhamnose by the method of Dische et al., J. Biol. Chem. (1948) 175: 595 and the phosphate by the method of Chen et al., Anal. Chem. (1956) 28; 1756. In the case of the polysaccharide of S. pneumoniae type 14 and the oligosaccharide which is derived from it by fragmentation, the [hexose]/[hexosamine] ratios are substantially identical. The same is true for the [rhamnose]/[hexose] and [phosphate]/[hexose] ratios respectively considered in the case of S. pneumoniae types 18C and 23F.

Analysis, by NMR spectrometry, of the oligosaccharides does not detect signals which indicate heterogeneity in the repeating units and thus show that the oligosaccharides consist of an intact repeating unit.

Finally, with regard to the mean MW of the oligosaccharides, the results are as follows:

| Strain | Mean MW of the polysaccharide (expressed in $K_D$) | Mean MW of the oligosaccharide (expressed in $K_b$) |
| --- | --- | --- |
| N. meningitidis A | 0.15 | 0.66 |
| S. pneumoniae 1 | 0.04 | 0.72 |
| S. pneumoniae 14 | 0.01 | 0.72 |
| S. pneumoniae 18C | 0.03 | 0.75 |
| S. pneumoniae 19F | 0.04 | 0.67 |
| S. pneumoniae 23F | 0.07 | 0.57 |

EXAMPLE 6

Preparation of an Oligosaccharide Vi of S. typhi/B Subunit of the Cholera Toxin Conjugate 6a) Introduction of an $NH_2$ group into the oligosaccharide Vi.

A freeze-dried product of the oligosaccharide Vi, as obtained in Example 1, is taken up in a phosphate buffer, pH 8, in an amount of 10 mg/ml. To this preparation are added diaminohexane and $NaCNBH_2$ in solutions; each to a final concentration of 12.5 mg/ml. The reaction is continued for 6 days at room temperature. The preparation is then dialysed against water and freeze-dried.

It is checked by assay according to the method of Shnyder et al., Anal. Biochem. (1975) 64: 284, that the $NH_2$ groups have indeed been introduced. Likewise, it is shown, by assay according to Hestrin, that the O-acetyl groups are still preserved.

6b) Introduction of a reactive functional group

The freeze-dried product obtained in 6a) is taken up in solution in an amount of 40 mg/ml. To 20 ml of this preparation are added 80 ml of a solution at 40 mg/ml of disuccinimidyl suberate (DSS) in dimethyl sulphoxide (DMSO). The reaction is continued for one hour at room temperature. The preparation is then precipitated in a mixture of DMSO/dioxane.

6c) Conjugation

The precipitate obtained in 6b) is taken up in a 0.5 M NaCl solution in an amount of 40 mg/ml. In parallel, a solution of B subunit of the cholera toxin is prepared (Tayot et al., Eur. J. Biochem. (1981) 113: 249) in 0.2 M phosphate buffer, pH 6.5, in an amount of 10 mg/ml.

The two solutions thus prepared are mixed together. The oligosaccharide/protein weight ratio is about 1. The reaction is continued at room temperature for 15 hours.

6d) Purification

The mixture is then filtered on an ultrafiltration minicartridge (Millipore) equipped with a membrane whose separation threshold is $5 \cdot 10^4$ daltons in order to remove the noncoupled protein and oligosaccharide. The retentate is washed in 0.3 M NaCl and then preserved in an amount of 200 µg/ml in NaCl 8/1000, merthiolate 1/10,000, at 4° C., after sterile filtration.

EXAMPLE 7

Preparation of Oligosaccharide/Tetanus Anatoxin Conjugates

The oligosaccharides as obtained from the polysaccharides of S. pneumoniae types 14 and 23F in Example 5, as well as the oligosaccharide obtained from the polysaccharide Vi of S. typhi in Example 1, are conjugated, the procedure being carried out in a manner similar to the procedure presented in Example 6 and the B subunit of the chlolera toxin being replaced by the tetanus anatoxin prepared according to the method of Mueller and Miller, J. Bact. (1954) 67: 671.

The conjugates obtained from oligosaccharides of S. pneumoniae are preserved at 250 µg/ml.

EXAMPLE 8

Demonstration of the Immunogenicity of the Conjugates

OF1 mice (IFFA Credo) are divided into batches of 8. Each mouse from a batch receives 0.5 ml of one of the solutions prepared in Examples 6 and 7 or in parallel, 0.5 ml of the corresponding native polysaccharides. The injections are performed subcutaneously. These injections are repeated 14 days later. In parallel, a control batch receives only physiological saline.

14 and 28 days after the first injection, a first blood sample is collected and the anti-polysaccharide antibodies IgG are titrated by ELISA assay (the titre plates are coated with nonfragmented polysaccharide). The antibody level after 14 and 28 days shows that the conjugates are immunogenic. In each of the cases, the antibody level is higher than that induced by the corresponding native polysaccharide. Furthermore, a rebound effect, characteristic of a T-dependent antigen, is observed.

EXAMPLE 9

Vaccinal Pharmaceutical Composition Comprising Conjugates as Active Ingredients

The oligosaccharides Vi of S. typhi/tetanus anatoxin conjugates obtained according to Example 7 are formulated in a vaccinal dose of 0.5 ml intended to be injected into man by the subcutaneous route. The composition per dose being:

| - Oligosaccharides Vi of *S. typhi* conjugates | 10 µg |
| --- | --- |
| - Phosphate buffer at pH 7 | 475 µg (as PO$_4$ ions) |
| - NaCl | 4250 µg |
| - Merthiolate | 0.05 µg |
| - Water for injections | qs 0.5 ml |

What is claimed is:

1. An oligosaccharide which has preserved the labile functional groups and the structure of the repeating units of an antigenic polysaccharide obtained from a pathogenic agent, wherein said polysaccharide has repeating units containing labile functional groups and wherein said oligosaccharide is in the form of a conjugate or is bound to a carrier, said oligosaccharide having been prepared by (i) subjecting said polysaccharide to an oxidation-reduction depolymerization reaction, (ii) recovering the resulting oligosaccharide and (iii) coupling said oligosaccharide with a conjugation partner or with a carrier so as to obtain said oligosaccharide in the form of a conjugate or bound to a carrier.

2. The oligosaccharide of claim 1 wherein said antigenic polysaccharide obtained from said pathogenic agent is a capsular polysaccharide obtained from a pathogenic bacterium or fungus.

3. The oligosaccharide of claim 2 wherein said pathogenic bacterium is of a genus selected from the group consisting of Staphylococcus, Streptococcus, Klebsiella, Salmonella, Escherichia, Neisseria, Shigella and Haemophilus.

4. The oligosaccharide of claim 2 wherein said pathogenic bacterium is selected from the group consisting of Staphylococcus, Streptococcus, Klebsiella, Salmonella, Neisseria, Shigella, and Haemophilus.

5. A process for the preparation of an oligosaccharide which has preserved the labile functional groups and the structure of the repeating units of an antigenic polysaccharide obtained from a pathogenic agent, said polysaccharide having repeating units containing labile functional groups and said oligosaccharide being in the form of a conjugate or being bound to a carrier, said process comprising (i) subjecting said antigenic polysaccharide to an oxidation-reduction depolymerization reaction in an aqueous solution with an oxidation-reduction agent, (ii) recovering the resulting oligosaccharide and (iii) coupling said oligosaccharide with a conjugation partner or with a carrier so as to obtain said oligosaccharide in the form of a conjugate or bound to a carrier.

6. The process of claim 5 wherein said oxidation-reduction depolymerization reaction is carried out in the presence of an oxidation-reduction agent selected from ascorbic acid and hydrogen peroxide.

7. The process of claim 5 wherein said oxidation-reduction depolymerization reaction is carried out in the presence of an oxidation-reduction agent selected from ascorbic acid and hydrogen peroxide, and in the presence of an iron or copper salt.

8. The oligosaccharide of claim 1 wherein said conjugation partner is selected from the group consisting of a peptide, a protein and an organic polymer.

9. The oligosaccharide of claim 6 wherein said conjugation partner is selected from the group consisting of Pertussis toxin, a cholera toxin, a tetanus toxin and a diphtheria toxin.

10. The oligosaccharide of claim 1 incorporated into liposomes.

11. A pharmaceutical composition comprising a pharmaceutically acceptable carrier and, as an active ingredient, at least one oligosaccharide which has preserved the labile functional groups and the structure of the repeating units of an antigenic polysaccharide obtained from a pathogenic agent, said oligosaccharide being in the form of a conjugate or bound to a carrier, and said polysaccharide having repeating units containing labile functional groups, wherein said oligosaccharide is prepared by a process comprising (i) subjecting said polysaccharide to an oxidation-reduction depolymerization reaction, and (ii) recovering the resulting oligosaccharide and (iii) coupling said oligosaccharide with a conjugation partner or with a carrier so as to obtain said oligosaccharide in the form of a conjugate or bound to a carrier.

12. A method of vaccinating an individual comprising administering to said individual a composition comprising an oligosaccharide which has preserved the labile functional groups and the structure of the repeating units of an antigenic polysaccharide obtained from a pathogenic agent, said oligosaccharide being prepared by a process comprising (i) subjecting said polysaccharide to an oxidation-reduction depolymerization reaction, and (ii) recovering the resulting oligosaccharide and (iii) coupling said oligosaccharide with a conjugation partner or with a carrier so as to obtain said oligosaccharide in the form of a conjugate or bound to a carrier.

13. The process of claim 5, wherein said conjugation partner is a protein and wherein step (iii) comprises:

a) reacting said oligosaccharide with diaminohexane in the presence of a cyanoborohydride, b) reacting the compound obtained in step a) with disuccinimidyl substrate in the presence of dimethyl sulfoxide, and c) reacting the compound obtained in b) with said protein.

14. A process for conjugating an oligosaccharide with a protein, comprising:

a) reacting said oligosaccharide with diaminohexane in the presence of cyanoborohydride, b) reacting the compound obtained in step a) with disuccinimidyl suberate in the presence of dimethyl sulfoxide, and c) reacting the compound obtained in b) with said protein.

15. The process of claim 14, wherein said oligosaccharide is obtained by depolymerization of a polysaccharide obtained from a pathogenic agent.

16. The process of claim 15, wherein said pathogenic agent is a bacterium or a fungus.

17. The process of claim 16, wherein said bacterium is of a genus selected from the group consisting of Staphylococcus, Streptococcus, Klebsiella, Salmonella, Escherichia, Neisseria, Shigella and Haemophilus.

18. The process of claim 17 wherein said bacterium is selected from the group consisting of *S. typhi*, *S. pneumoniae*, *N. meningitidis* and *H. influenzae*.

19. An oligosaccharide which has preserved the labile functional groups and the structure of the repeating units of an antigenic polysaccharide obtained from a pathogenic agent, wherein said polysaccharide has repeating units containing labile functional groups and wherein said oligosaccharide is in the form of a conjugate or is bound to a carrier, said oligosaccharide having been prepared by (i) subjecting said polysaccharide to an oxidation-reduction depolymerization reaction at a pH in the range of 3 to 8.5 and a temperature in the range of 4 to 60° C., (ii) recovering the resulting oligosaccharide and (iii) coupling said oligosaccharide with a conjugation partner or with a carrier so as to obtain said oligosaccharide in the form of a conjugate or bound to a carrier.

20. An oligosaccharide of claim 19, wherein said reaction is carried out in the presence of an oxidation-reduction agent selected from the group consisting of ascorbic acid and hydrogen peroxide.

21. An oligosaccharide according to claim 20 wherein said reaction is carried out in the presence of at least one of a soluble salt of iron and a soluble salt of copper.

22. A pharmaceutical composition comprising a pharmaceutically acceptable carrier and an oligosaccharide according to claim 19.

23. A pharmaceutical composition comprising a pharmaceutically acceptable carrier and an oligosaccharide according to claim 20.

24. A pharmaceutical composition comprising a pharmaceutically acceptable carrier and an oligosaccharide according to claim 21.

25. A method of vaccinating an individual against pathogens comprising administering to an individual in need of said vaccinating a pharmaceutical composition according to claim 22.

26. A method of vaccinating an individual against pathogens comprising administering to an individual in need of said vaccinating a pharmaceutical composition according to claim 23.

27. An oligosaccharide of claim 1, wherein said reaction is carried out in the presence of an oxidation-reduction agent selected from the group consisting of ascorbic acid and hydrogen peroxide.

28. A pharmaceutical composition comprising a pharmaceutically acceptable carrier and an oligosaccharide according to claim 27.

29. A method of vaccinating an individual against pathogens comprising administering to an individual in need of said vaccinating a pharmaceutical composition according to claim 28.

30. A process for the preparation of an oligosaccharide which has preserved the labile functional groups and the structure of the repeating units of an antigenic polysaccharide obtained from a pathogenic agent, said polysaccharide having repeating units containing labile functional groups and said oligosaccharide being in the form of a conjugate or being bound to a carrier, said process comprising (i) subjecting said antigenic polysaccharide to an oxidation-reduction depolymerization reaction in an aqueous solution with an oxidation-reduction agent, at a pH in the range of 3 to 8.5 and at a temperature in the range of 4 to 60° C., (ii) recovering the resulting polysaccharide and (iii) coupling said oligosaccharide with a conjugation partner or with a carrier so as to obtain said oligosaccharide in the form of a conjugate or bound to a carrier.

31. A process according to claim 30 wherein said reaction is carried out in the presence of an oxidation-reduction agent selected from ascorbic acid and hydrogen peroxide.

32. The process of claim 31 wherein said oxidation-reduction depolymerization reaction is carried out in the presence of an oxidation-reduction agent selected from ascorbic acid and hydrogen peroxide, and in the presence of an iron or copper salt.

33. The composition according to claim 11 wherein said labile functional group is an acetyl group.

34. The composition according to claim 11 wherein said labile functional group is a pyruvate group.

35. The composition according to claim 11 wherein said labile functional group is a phosphate group.

36. The oligosaccharide of claim 1 wherein said pathogenic agent is *S. tryphi.*

37. The oligosaccharide of claim 1 wherein said pathogenic agent is *S. pueumoniae.*

38. The oligosaccharide of claim 1 wherein said pathogenic agent is *N. meningitidis.*

39. The oligosaccharide of claim 1 wherein said pathogenic agent is *H. influenza.*

40. The method of claim 12 wherein said labile functional group is an acetyl group.

41. The method of claim 12 wherein said labile functional group is a pyruvate group.

42. The method of claim 12 wherein said labile functional group is a phosphate group.

43. The method of claim 12 wherein said pathogenic agent is *S. typhi.*

44. The method of claim 12 wherein said pathogenic agent is *S. pneumoniae.*

45. The method of claim 12 wherein said pathogenic agent is *N. meningitidis.*

46. The method of claim 12 wherein said pathogenic agent is *H. influenza.*

47. The process of claim 5 wherein said antigenic polysaccharide is present in a concentration of 0.5–50 mg/ml.

48. The process of claim 5 wherein said oxidation-reduction depolymerization reaction is performed in the presence of ascorbic acid.

49. The process of claim 48 wherein ascorbic acid is present in a concentration of 0.01–25 mg/ml.

50. The composition of claim 11 wherein said polysaccharide of (i) is present in a concentration of 0.5–50 mg/ml.

51. The composition of claim 11 wherein said oxidation-reduction depolymerization reaction is performed in the presence of ascorbic acid.

52. The composition of claim 51 wherein said ascorbic acid is present in a concentration of 0.01–25 mg/ml.

53. An oligosaccharide according to claim 1 wherein said polysaccharide is a capsular polysaccharide.

54. A process according to claim 5 wherein said polysaccharide is a capsular polysaccharide.

55. A pharmaceutical composition according to claim 11 wherein said polysaccharide is a capsular polysaccharide.

56. A method of vaccination according to claim 12 wherein said polysaccharide is a capsular polysaccharide.

57. The process of claim 15 wherein said polysaccharide is a capsular polysaccharide.

58. The oligosaccharide of claim 19 wherein said polysaccharide is a capsular polysaccharide.

59. The process of claim 5 wherein said pathogenic agent is a pathogenic bacterium selected from the group consisting of Staphylococcus, Streptococcus, Klebsiella, Salmonella, Neisseria, Shigella and Haemophilus.

60. The pharmaceutical composition of claim 11 wherein said pathogenic agent is a pathogenic bacterium selected from the group consisting of Staphylococcus, Streptococcus, Klebsiella, Salmonella, Neisseria, Shigella and Haemophilus.

61. The method of claim 12 wherein said pathogenic agent is a pathogenic bacterium selected from the group consisting of Staphylococcus, Streptococcus, Klebsiella, Salmonella, Neisseria, Shigella and Haemophilus.

62. The process of claim 59 wherein said oxidation-reduction reaction is carried out in the presence of an oxidation-reduction agent selected from ascorbic acid and hydrogen peroxide.

63. The process of claim 59 wherein antigenic polysaccharide is present in a concentration of 0.5–50 mg/ml.

64. The process of claim 59 wherein the ascorbic acid is present in a concentration of 0.01–25 mg/ml.

65. The process of claim 59 wherein said polysaccharide is a capsular polysaccharide.

* * * * *